(12) United States Patent
Hurst et al.

(10) Patent No.: US 7,575,926 B1
(45) Date of Patent: Aug. 18, 2009

(54) METHOD OF IDENTIFICATION OF COMPOUNDS EFFECTIVE AGAINST SUPPRESSED CANCER CELLS

(75) Inventors: Robert E. Hurst, Oklahoma City, OK (US); Michael A. Ihnat, Tuttle, OK (US); Kimberly D. Kyker, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 183 days.

(21) Appl. No.: 11/642,313

(22) Filed: Dec. 19, 2006

Related U.S. Application Data

(60) Provisional application No. 60/751,698, filed on Dec. 19, 2005.

(51) Int. Cl.
*C12N 5/06* (2006.01)
*C12N 5/08* (2006.01)

(52) U.S. Cl. .................. 435/374; 435/375; 435/377; 435/395

(58) Field of Classification Search ............... None
See application file for complete search history.

(56) References Cited

U.S. PATENT DOCUMENTS

2006/0074041 A1* 4/2006 Johnston et al. ............ 514/44

FOREIGN PATENT DOCUMENTS

| WO | WO 00/06088 | * | 2/2000 |
| WO | WO0240717 | * | 5/2002 |
| WO | WO2005107743 | * | 11/2005 |

OTHER PUBLICATIONS

Abstract if Clarkson et al (Cancer, 1965, vol. 18, pp. 1189-1213).*
Abstract of Miller et al (Clin Exp Metastasis, 1998, vol. 16, pp. 480-486).*
Danson et al, Cancer chemother Pharmacol, 2007, vol. 10, pp. 851-861).*
Hurst, R., et al., "Matrix-dependent Plasticity of the Malignant Phenotype of Bladder Cancer Cells", *Anticancer Research* 23: 3119-3128; 2003.
Kyker, K., et al., "A Model for 3-dimensional growth of bladder cancers to investigate cell-matrix interaction", *Urologic Oncology: Seminars and Orginal Investigation* 21: 255-261, 2003.
Hurst, R., et al., "A novel multidrug resistance phenotype of bladder tumor cells grown on Matrigel or SIS gel", *Science Direct Cancer Letters* 217: 171-180, 2005.

* cited by examiner

*Primary Examiner*—Karen A Canella
(74) *Attorney, Agent, or Firm*—Dunlap Codding, P.C.

(57) ABSTRACT

A method for identifying compounds capable of targeting suppressed cancer cells, the method including the steps of comparing the response to a test compound of cancer cells grown on a suppressing cell support matrix which causes suppression of a malignant phenotype in a growing cancer cell and on a non-suppressing cell support matrix.

15 Claims, 10 Drawing Sheets

METHOD OF IDENTIFICATION OF COMPOUNDS EFFECTIVE AGAINST SUPPRESSED CANCER CELLS

CROSS-REFERENCE TO RELATED APPLICATIONS

This application claims priority under 35 U.S.C. § 119(e) of U.S. Provisional Application Ser. No. 60/751,698, filed on Dec. 19, 2005, entitled "METHOD OF IDENTIFICATION OF COMPOUNDS EFFECTIVE AGAINST SUPPRESSED CANCER CELLS," which is hereby expressly incorporated by reference in its entirety.

STATEMENT REGARDING FEDERALLY SPONSORED RESEARCH OR DEVELOPMENT

Some aspects of this invention were made in the course of Grants 1 R01 CA75822 and DK R01 069808 awarded by the National Institute of Health and therefore the Government has certain rights in some aspects of this invention.

BACKGROUND

Most cancer deaths are caused by metastases, which are secondary tumors from cancer cells that have broken off from the primary tumor and now are surviving at a distant site. Often these exist as micrometastases consisting of one or a few cells that are not growing or are growing very slowly. Eventually some of the micrometastases will begin to grow rapidly, forming tumors which eventually kill the patient. Micrometastases are notoriously resistant to traditional chemotherapeutic agents because the cells are not actively growing.

Currently, the drug development system for developing anticancer drugs is based on finding compounds that kill growing tumors. The initial step in developing an anticancer drug involves the screening of compounds against cancer cells growing in ordinary tissue culture on plastic. In vitro growth on plastic neglects the true physiological conditions under which tumors grow in the body, i.e., in contact with extracellular matrix. The extracellular matrix in living tissues is the supporting material on which all cells grow and which interacts with cells to regulate their growth and how they assume their mature functions. Cancer cells remodel the extracellular matrix to be more conducive to growth of the cancer cells, and this process seems to represent a major requirement for them to be able to form a tumor.

For example, about 60,000 new cases of bladder cancer occur each year in the U.S. with about 13,000 deaths, placing it 5th overall in cancer incidence. In the United States, 98% of bladder cancers arise from the transitional epithelium of the bladder (transitional cell carcinoma, TCC). The general perception that bladder cancer is not serious is false. Some 15-25% of cases are invasive at diagnosis with one-fourth already having metastasized and with up to half developing metastatic tumors within two to three years. The 5-year survival of patients with metastatic bladder cancer is very low, about 20% with about a six-month median survival for even the most aggressive therapies. Of the 80-85% that are papillary, recurrence is high, up to 70% within 5 years in some studies, and of these, some 15%-25% will progress to invasive bladder cancer. Therapy achieves few cures, whether with BCG chemotherapy or neoadjuvant chemotherapy. The reasons for the high recurrence rate of bladder cancer are not known entirely, however, three mechanisms are suggested including underdiagnoisis by cystoscopy, a widespread "field defect" with continued promotion of new tumors or suppression of malignant cells, preventing their growth for a time.

To this end, the present invention is directed to a novel approach for identifying compounds capable of targeting living, phenotypically suppressed cancer cells.

DETAILED DESCRIPTION OF THE INVENTION

The present invention contemplates a novel method for identifying compounds capable of targeting and attacking suppressed cancer cells. As used herein, the term "suppressed" refers to cells which are not expressing their malignant phenotype. An example of a suppressed cancer cell includes a micrometastatic cell. Previous studies have shown that when cancer cells are grown on an extracellular matrix preparation derived from normal tissue, the malignant phenotype is suppressed and they radically change their appearance and growth characteristics to appear more normal. Cancer cells growing on this normal matrix are representative of suppressed micrometastatic cancer cells (cancer cells having a suppressed malignant phenotype). Finding compounds that are more active against cancer cells cultured on a normal matrix than they are against cells growing on plastic (or other "permissive" media) will identify compounds active against phenotypically suppressed micrometastases.

According to the present invention, test compounds are screened for the ability to target suppressed cancer cells that are representative of micrometastases and of recurrent tumors. The present invention presents the ability to develop anticancer drugs that will cure micrometastatic disease which is the true killer of many cancer patients. Additionally, the present invention allows rapid screening of compounds that have weak activity against established primary tumors, but which are also more effective against micrometastatic disease.

The present invention is applicable in cancer research and drug development and solves the problem of providing a model that is more relevant to the biology of micrometastatic cells than is the conventional approach. Moreover, the strategy employed in the present invention of screening compounds specifically targets development of compounds that will be active against metastatic tumors and recurrent tumors.

A primary advantage of the present invention is, by initially screening using a matrix that suppresses the malignant phenotype, the compounds identified will be more active against the suppressed phenotype. This testing regimen provides for optimization of the development of novel anticancer drugs that specifically target recurrent and micrometastatic disease.

Figure 4:
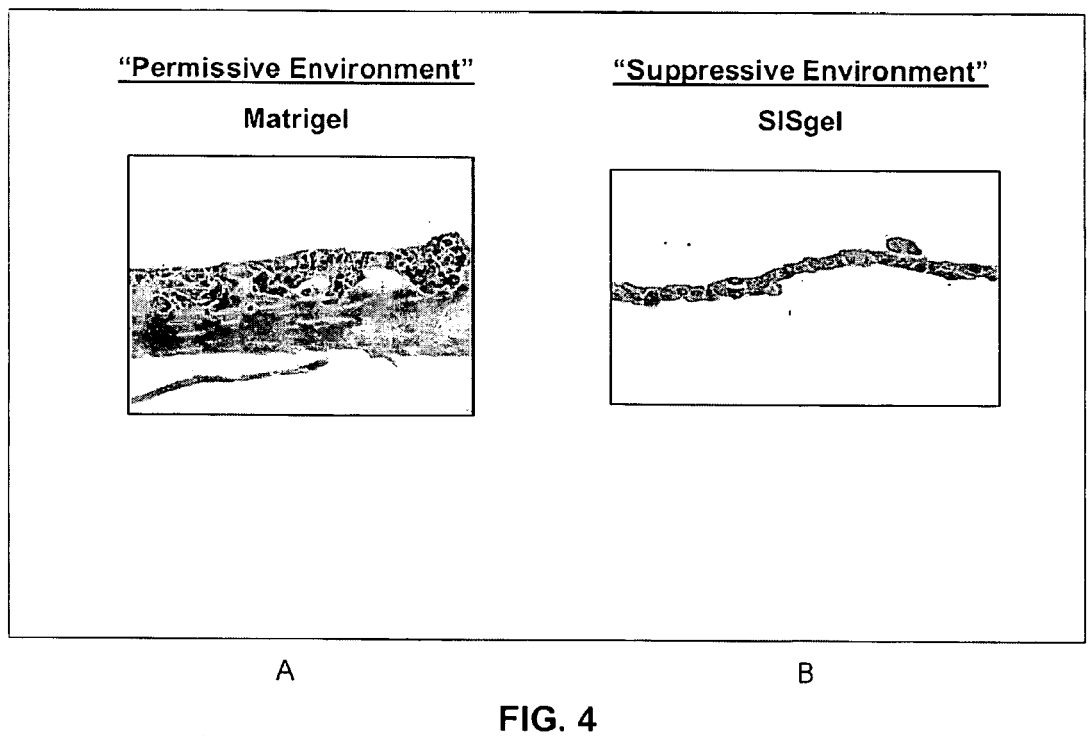
FIG. 4A is a micrograph showing cell growth on a non-suppressing cell support matrix.
FIG. 4B is a micrograph showing cell growth on a suppressing cell support matrix.
Figure 7:
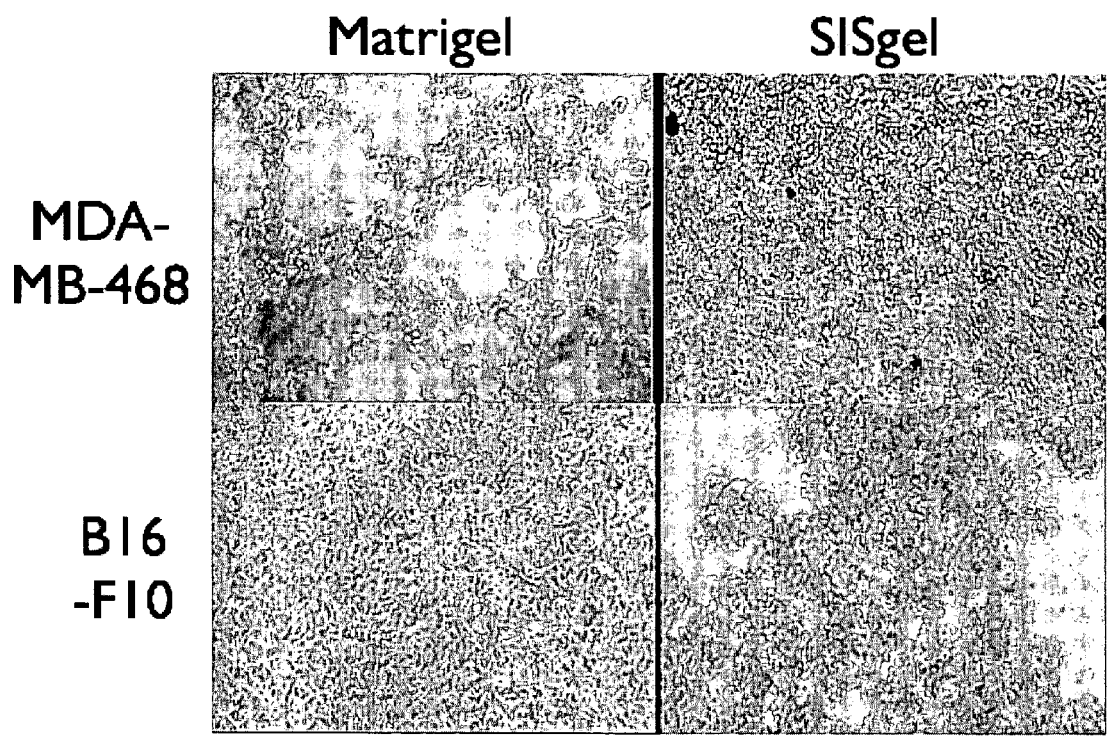
FIG. 7 is a micrograph showing morphology changes of MDA-MD-468 breast cancer cells and B16-F10 melanoma cells on Matrigel and SISgel.

Referring now to the drawings and more particularly to FIG. 1, FIGS. 4A and 4B, and FIG. 7, the method for identifying a compound which preferentially targets cancer cells having a suppressed malignant phenotype includes the steps of, in a first culture system, providing a suppressing cell support matrix which causes suppression of a malignant phenotype in a growing cancer cell. Examples of suppressing cell support matrices include, but are not limited to, SISgel, Humatrix, and similar support media (FIGS. 4B and 7). Shown in FIG. 4B is growth of J82 cells from a highly aggressive tumor wherein growth on SISgel suppresses the malignant phenotype and models conditions found by metastasizing cells which must overcome suppressive effects of local extracellular matrix. Shown in FIG. 7 is growth of MDA-MB-468 breast cancer cells and B16-F10 skin tumor cells (metastatic murine melanoma) wherein growth on SISgel suppresses the malignant phenotype and models conditions found by metastasizing cells which must also overcome suppressive effects of local extracellular matrix (i.e., Matrigel). Examples of other cell lines exhibiting similar behavior as that of J82, MDA-MB-468, and B16-F10 cell lines and in which the test compounds have been shown to be active against include RT4 cells, TCCSUP cells, and 5637 cells.

The method further includes the step of providing a cell-nutrient mixture having a quantity of cancer cells disposed in a nutrient media. Examples of cancer cells which may be used include, but are not limited to, bladder cancer cells, liver cancer cells, breast cancer cells, lung cancer cells, prostate cancer cells, colon cancer cells, melanoma, or other transitional cancer cells, squamous cancer cells, small cancer cells, medulary cancer cells, adenocarcinomas, basal cell carcinomas or any other metastatic cell line, micrometastatic cell lines, or other cell lines derived from a secondary tumor. A first portion of the cell-nutrient mixture is combined with (layered on top of) the suppressing cell support matrix thereby forming a suppressing matrix-cell mixture (bilayered system). The suppressing matrix-cell mixture (bilayered system) is incubated for a period of time to allow growth of the cells while causing suppression of the malignant phenotype in the cancer cells thereby forming a suppressed cancer cell culture. A test compound is added to the suppressed cancer cell culture forming a treated suppressed culture. The treated suppressed culture is incubated for a period of time forming an incubated treated suppressed culture.

The method of the present invention further includes the step of, in a second culture system, providing a non-suppressing cell support matrix which allows expression of a malignant phenotype in a growing cancer cell. Examples of non-suppressing cell support matrices include, but are not limited to, plastic (as known to those of ordinary skill in the art), Matrigel and similar support media. (FIGS. 4A and 7). Shown in FIGS. 4A and 7, respectively, is growth of 382, MDA-MB-468, and B16-F10 cells from highly aggressive tumors on Matrigel recapitulating in vivo phenotype of the original tumor. A second portion of the cell-nutrient mixture is combined with (layered on top of) the non-suppressing cell support matrix forming a non-suppressing matrix-cell mixture (bilayered system). The non-suppressing matrix-cell mixture (bilayered system) is incubated for a period of time to allow growth of the cells and expression of the malignant phenotype in the cancer cells thereby forming a non-suppressed cancer cell culture. The test compound is added to the non-suppressed cancer cell culture forming a treated non-suppressed culture. The treated non-suppressed culture is incubated for a period of time thereby forming an incubated treated non-suppressed culture. The number (or survival) of suppressed cancer cells in the incubated treated suppressed culture is compared with the number (or survival) of non-suppressed cancer cells in the incubated treated non-suppressed culture.

Preferably, the method further includes the step of concluding that the test compound is positive (i.e., preferentially targets suppressed cancer cells) when the number or survival of cancer cells in the incubated treated non-suppressed culture exceeds the number or survival of cancer cells in the incubated treated suppressed culture or, conversely, when cell mortality of the suppressed culture exceeds the cell mortality in the non-suppressed culture. For example, a threshold for concluding that suppressed cancer cells are preferentially targeted is when the number (or survival) of cancer cells in the incubated treated non-suppressed culture is at least twice the number (or survival) of cancer cells in the incubated treated suppressed culture. A positive test compound is preferably confirmed via a full-dose response curve performed in a different, non-suppressing cell-support matrix preparation such as, for example, Matrigel, plastic, or other material or media for screening increased activity of the test compound when compared to the test compound's activity in the suppressing cell support matrix.

In another embodiment, the present invention contemplates a method for identifying a compound which preferentially targets cancer cells having a suppressed malignant phenotype. The method includes the steps of providing a suppressed cancer cell culture comprising actively growing cancer cells which have a malignant phenotype, wherein the malignant phenotype of the cancer cells is suppressed. Examples of cancer cells include any of the cancer cells set forth hereinabove.

Where used herein, the term "survival" refers to the percentage of cells which are alive after a course of treatment. Conversely, "mortality" refers to the percentage of cells which have died after a course of treatment.

The method further includes the step of providing a non-suppressed cancer cell culture comprising actively growing cancer cells which have the malignant phenotype, wherein the malignant phenotype of the cancer cells is expressed. The suppressed cancer cell culture and the non-suppressed cancer cell culture are each treated with a test compound (as set forth hereinabove) and incubated. The number or survival of cancer cells in the treated suppressed cancer cell culture is compared with the number or survival of cancer cells in the treated non-suppressed cancer cell culture or, conversely, when cell mortality of the suppressed culture exceeds the cell mortality in the non-suppressed culture.

In addition, the present invention further includes the step of concluding that the test compound preferentially targets cancer cells having suppressed malignant phenotypes when the number or survival of cancer cells in the treated non-suppressed cancer cell culture exceeds the number or survival of cancer cells in the treated suppressed cancer cell culture.

The present invention further contemplates a kit comprising the suppressing cell support matrix, the non-suppressing cell support matrix, and the cell-nutrient mixture, wherein the cell-nutrient mixture and the suppressing and non-suppressing cell support matrices can be combined and incubated as described above.

In another embodiment, the present invention contemplates a kit wherein portions of the cell-nutrient mixture are pre-mixed with the cell-support matrices to form a suppressing matrix-cell mixture and a non-suppressing matrix-cell mixture which are refrigerated (or otherwise handled) for a period of time to prevent active cell growth. The mixtures may be plated for providing ready-to-use test cultures to which test compounds may be applied. As noted, each mixture, or each suppressing test culture and non-suppressing test culture may be refrigerated for suspension of cell growth until used in the methods described herein.

Figure 3A:
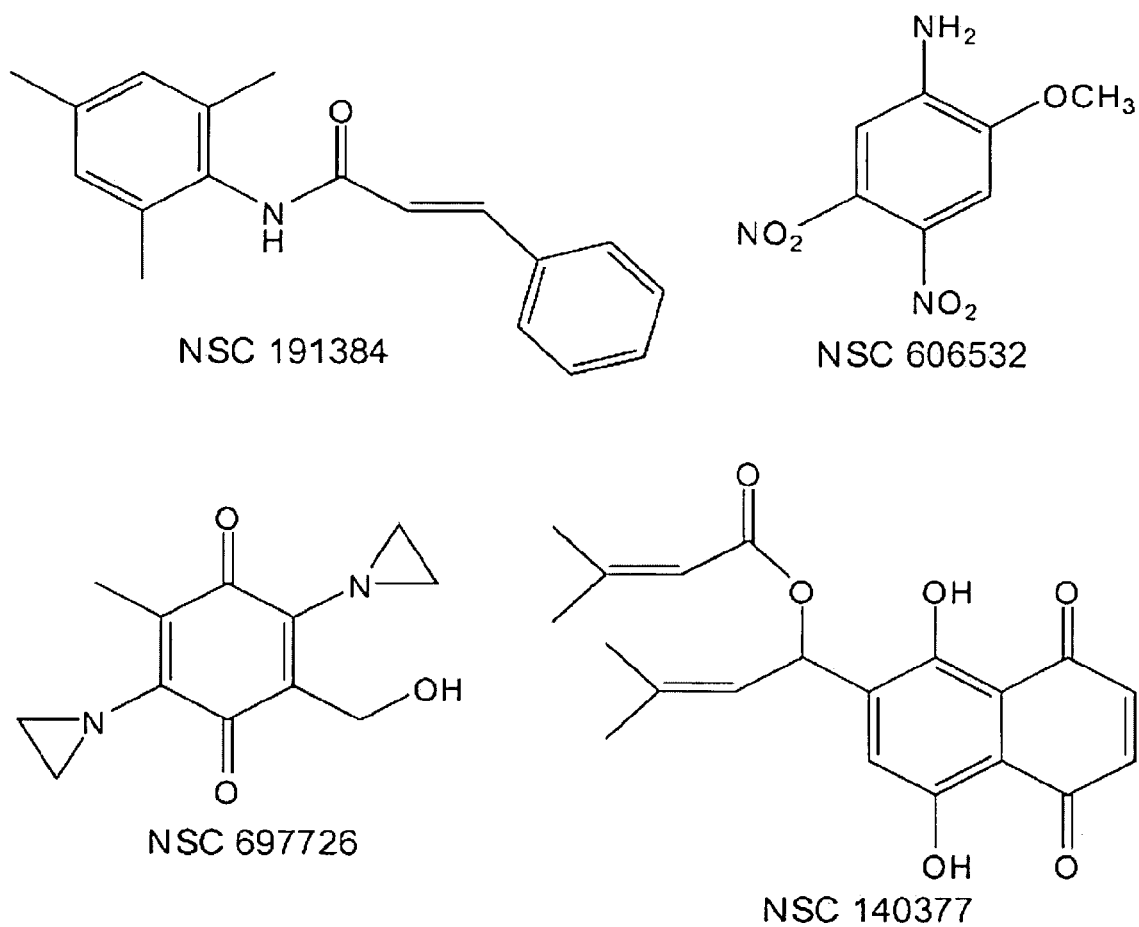
FIG. 3A shows chemical structures of four test compounds.
Figure 3B:
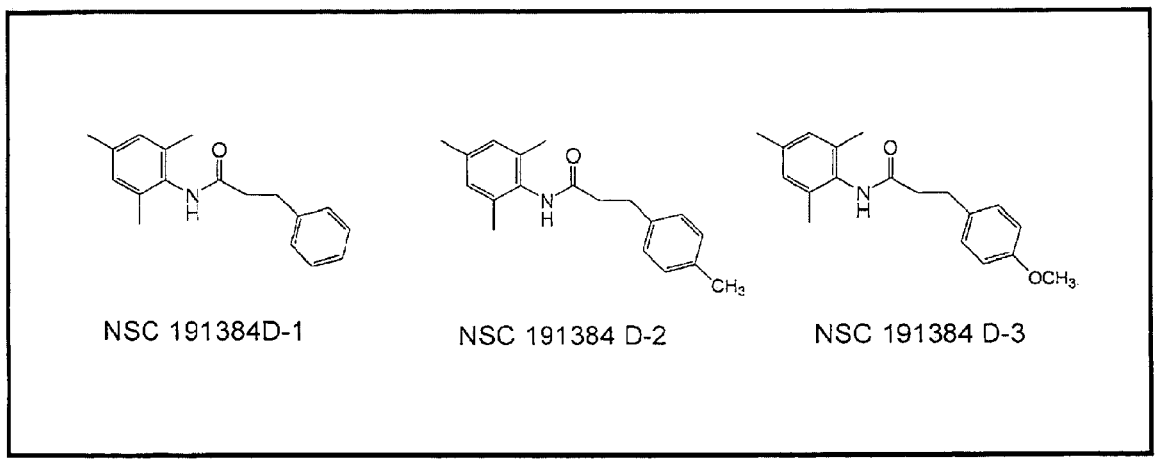
FIG. 3B shows chemical structures of three derivatives of Compound NSC191384 of FIG. 3A.
Figure 6:
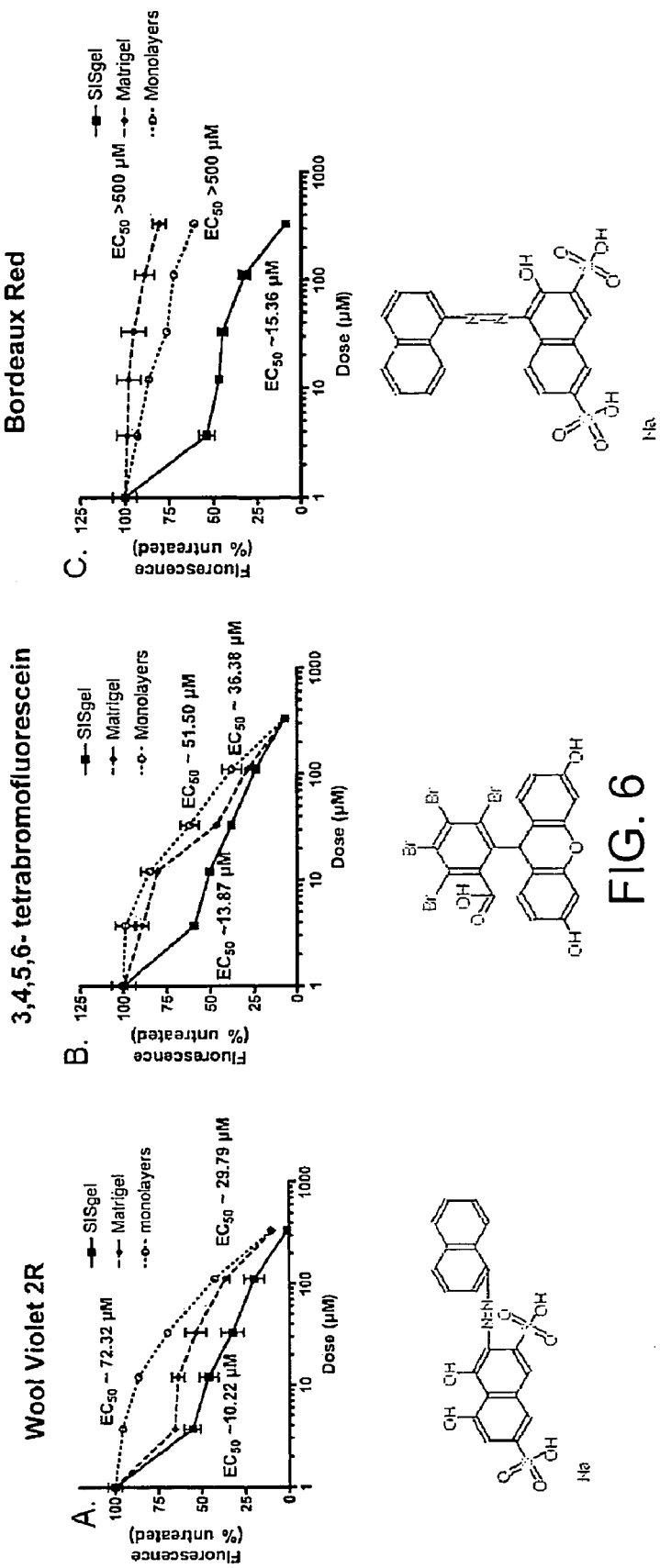
FIGS. 6A-6C are Full Dose-Response Curves identifying three lead compounds for attacking suppressed cancer cells.

The present invention further contemplates a method of treating bladder cancer, liver cancer, breast cancer, lung cancer, prostate cancer, colon cancer, melanoma, or any cancer including, but not limited to, those involving transitional cells, squamous cells, small cells, medulary cells, adenocarcinomas, and basal cell carcinomas, the method including administering a composition comprising one or more of the compounds selected from the group consisting of NSC191384, NSC19134D-1, NSC19134D-2, NSC19134D-3, NSC 606532, NSC 697726, and NSC140377, as identified in FIGS. 3A and 3B, Wool Violet 2R, 3,4,5,6-tetrabromofluorescein, and Bordeaux Red, as identified in FIGS. 6A-6C, to a subject in need thereof whereby, for example, the composition preferably further comprises a pharmaceutically acceptable carrier within which the compound is disposed.

While the invention is described herein in connection with certain embodiments and examples so that aspects thereof may be more fully understood and appreciated, it is not intended that the invention be limited to these particular embodiments and examples. On the contrary, it is intended that all alternatives, modifications and equivalents are included within the scope of the invention as defined herein. Thus the examples described herein, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention. Changes may be made in the formulation of the various compositions described herein or in the steps or the sequence of steps of the methods described herein without departing from the spirit and scope of the invention as described herein.

All references, articles, patents, and pending patent applications cited herein are hereby expressly incorporated herein in their entirety by reference.

Methods

Cell culture. All tissue culture media and supplements were from Invitrogen, Rockville, Md. Matrigel was obtained from Becton-Dickinson (Bedford, Mass.). SISgel was obtained from Cook Biotech (W. Lafayette, Ind.). TCC-SUP, J82, and 5637 cells were obtained from the American Type Culture Collection (ATCC).

Flank xenograft model. J82 cells stably expressing green fluorescent protein (GFP) were prepared as follows. pLE-GFP-C1 retrovirus (Clontech, Mountain View, Calif.) was co-transfected with the pVSV-G vector (Clontech, Mountain View, Calif.) which contains a viral envelope gene into the packaging cell line GP2-293 (Clontech, Mountain View, Calif.). Supernatant from the packaging cells containing the infective virus was collected every 24 hours for 4 days. Fluorescent target cells were made by infecting J82s, a urothelial transitional cell carcinoma cell line (ATCC, Manassas, Va.), with 1 ml of fresh, virus containing, supernatant/well containing 100,000 target cells along with 8 µg/ml of polybrene (Sigma Aldrich, St. Louis, Mo.). Each application of viral supernatant was filtered through a 0.4 µM syringe filter before application to target cells. Supernatant was removed and fresh virus containing media replenished on target cells every 24 hours until 4 changes of media were completed. Virus containing media was replaced with Minimum Essential Media, MEM, (Life Technologies, Carlsbad, Calif.) containing 1% nonessential amino acids, 1% L-glutamine, 1% sodium pyruvate and 10% Fetal Calf Serum, and cells were allowed to grow to 90% confluence. Stable transfects were selected through sequential sorting and enrichment of fluorescent cells using flow cytometry.

In sterile 500 µl centrifuge tubes, placed on ice, 100 µl of cell suspension was mixed with either 100 µl ice-cold prepared SISgel or ice-cold Matrigel and mixed well. The mix was immediately injected into either the right or left flank of a 5-week old nude mouse, nu/nu-nuBR, (Charles River Laboratories, Wilmington, Mass.). Caliper measurements of tumor size were taken every week for the length of the study as were fluorescent images. Images were visualized with the Lightool's LT-9900 system (Lightools, Encinitas, Calif.) with the EGFP filter set of 470 nm excitation filter and 515 nm viewing filter and captured with a Nikon DC290 digital camera. The area and intensity of the tumor was measured using Adobe Photoshop by first selecting the tumor area, then counting pixels above a threshold selected to eliminate background, non-tumor areas. The integrated intensity was calculated by multiplying the average intensity of detected pixels by the number of pixels detected.

Plating of cells for screening. Three-dimensional gel cultures with Matrigel were made by layering 50 µl of ice cold Matrigel into wells of a Costar 3610 white, clear bottom 96-well plates (Corning, Corning, N.Y.) allowed to gel at 37° C. Confluent cells were trypsinized with 1 ml 0.25% trypsin-1 mM EDTA, and 30,000 were added to wells containing the gelled matrices. The cells were fed with 50 µl of their respective media containing 10% fetal calf serum. To establish non-confluent monolayers, cells were plated at a cell density of 10,000/well 24 hours prior to drug treatments.

Screening of compounds. The National Cancer Institute Developmental Therapeutics Program (NCI DTP) diversity set of 1990 compounds[1] was obtained by material transfer agreement and was diluted to a final concentration of 166.7 µM in serum-containing media and placed onto cells for 72 hours at 37° C. and 5% $CO_2$. A marker of cell proliferation using the substrate 5-carboxyfluorescein diacetate acetoxymethyl ester (CFDA-AM) cleaved to fluorescein by non-specific cellular esterases was used. Briefly, media containing a final concentration of 5 µM CFDA-AM (Molecular Probes, Eugene, Oreg.) was added in PBS for two h at 37° C. Plates were then read by a FLUOstar Optima plate reader (BMG LABTECH, Durham, N.C.) using 385 nm excitation, 428 nm emission filter.

Dose-response relations of lead compounds. To 100 µl media on cells was added 100 µl of a 2× (666.7 µM) stock of either doxorubicin, tetrandrine or o-cresolphthalein in completed media in a single column in a 96-well plate. 1:3 dilutions were made from this highest dose by removing 66.7 µl into the next column of cells containing 133 µl media. Cells were incubated with drug for 72 hours, then the CFDA-AM assay completed as described above.

Data Analysis and Statistics.

Drug screening. The percent inhibition of cell proliferation (as determined by CFDA-AM cleavage) as compared to untreated cells was calculated for each drug in the wells of plates. The ratio of percent inhibition of the same drug of cells grown on SISgel as compared to non-confluent monolayers also was calculated. All library compounds were screened twice for consistency.

Dose-response relations. Data were graphed as percent inhibition of proliferation as compared to untreated cells and from this $EC_{50}$ values calculated using sigmoidal dose-response non-linear regression analysis (GraphPad Prism 4.0 software, San Diego, Calif.). Dose-response relation data were compared to one another using two-way ANOVA with Bonferroni post-test (GraphPad Prism 4.0 software, San Diego, Calif.).

EXAMPLES

SISgel (90 μl) is added to wells of a 96-well plate and allowed to gel. Cancer cells in 50 μl of nutrient (such as, for example, J82 bladder cancer cell, RT4 cancer cells, TCCSUP cancer cells, 5637 cancer cells, MDA-MB-468 breast cancer cells, or B16-F10 skin tumor (or any metastatic murine melanoma)) are added to each well and allowed to attach and grow. After 24 hours, the test compounds are added to wells at 10 μM concentration. The cells are allowed to grow in the presence of the test compound for 24 hours, at which time the number of cells (or survival or mortality) are estimated by a fluorometric method. In one embodiment, the fluorometric method is an assay performed using an esterase substrate, 5-carboxyfluorescein diacetate acetoxymethyl ester (CFDA) (available from Molecular Probes, Eugene, Oreg., USA), however, any suitable assay for measuring cell survival or mortality known by those of ordinary skill in the art may be used. Examples of fluorometers which can be used include, but are not limited to, FLUOStar Optima plate reader (BMG Biotech), FL600 fluorescent plate reader (Bio-Tek Instruments), Victor2 plate reader (Wallac), FluoroCount BF10000 fluorescent microplate reader (Packard), CytoFluor® 4000 (Applied Biosystems), Bio-Tek Synergy, BMG FLUOstar Galaxy and OPTIMA, PerkinElmer Victor™, PerkinElmer HTS 7000, TECAN SpectraFluor Plus, Thermo LabSystems Fluoroskan Ascent, and the like.

The cell number results are compared to those observed in cells grown conventionally on plastic in nearly confluent monolayers that show approximately the same growth rate as the cells on SISgel. In this embodiment, a greater than two-fold difference (SISgel:monolayer ratio, see FIG. 5, for example) in cell death (mortality) between cells grown on SISgel and on plastic (i.e., presence of at least twice as many living cells on the plastic culture) is interpreted as indicating that the compound is positive, i.e., it targets suppressed cells. In other embodiments, the ratio used may be, for example, less than two fold or greater than two fold as long as the cell number or survival on non-suppressing cell support matrix is greater than the number of cells on the suppressing cell support matrix. Preferably, each positive result is then confirmed by a full dose-response curve.

The dose-response curve of those test compounds that are confirmed as targeting cells growing on the suppressing cell support matrix are then determined in Matrigel, Vitrogen 100 (collagen gel), or any other non-suppressing cell support matrix, preferably wherein the cell support matrix is a cancer-derived matrix. Matrigel, for example, is a cancer-derived extracellular matrix preparation in which the cancer cells express the full malignant phenotype. Test compounds that show a greater effect on cells grown in SISgel than in Matrigel or on plastic (i.e., are positive) are then referred to as lead compounds. The lead test compounds can be administered shortly after metastatic tumors are established, identified, or purported to exist and are small and still likely in the suppressed state.

Results

Figure 1:
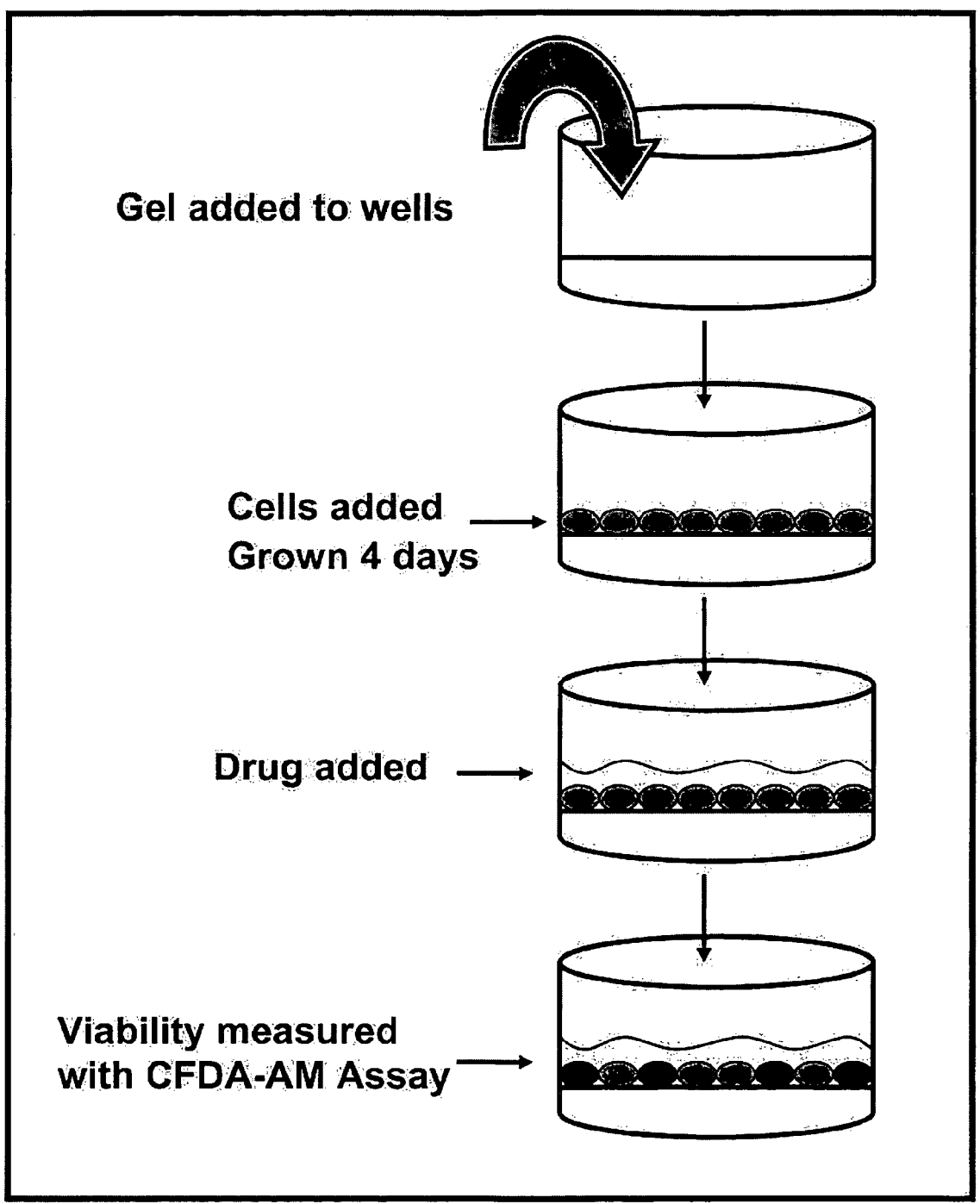
FIG. 1 is a pictorial representation of a test compound screening method of the present invention.
Figure 2:
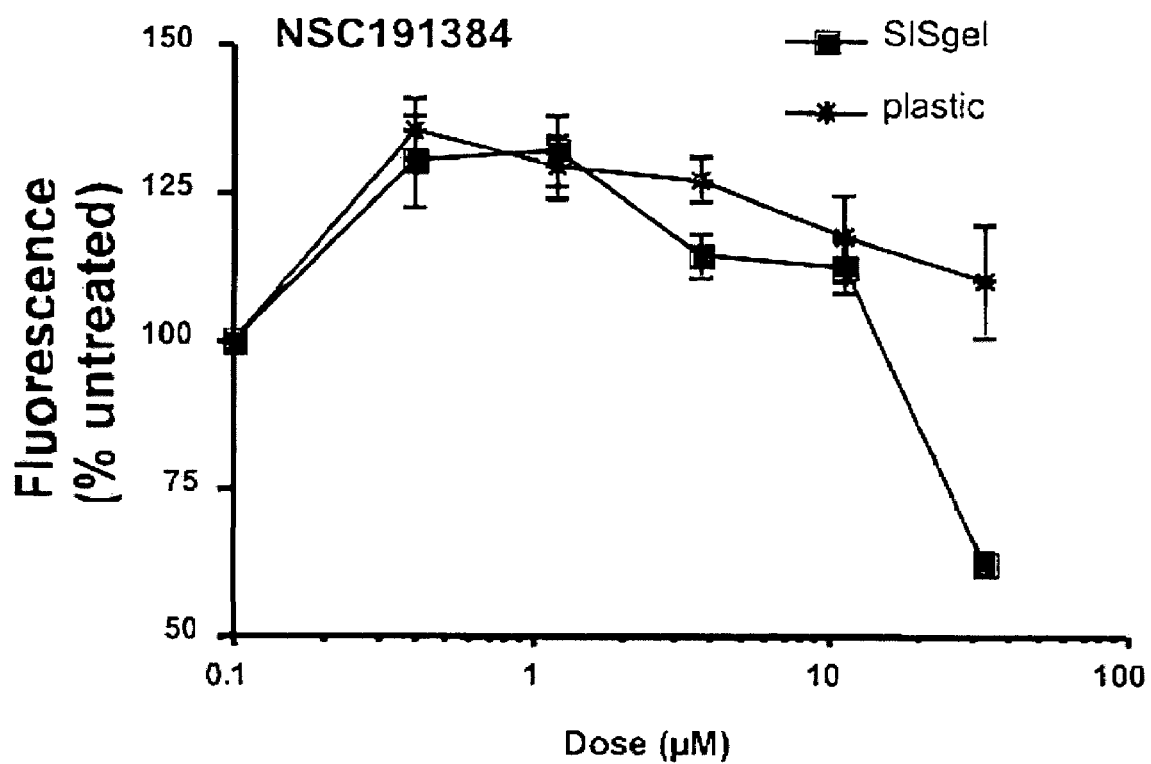
FIG. 2 is a graph of a Full Dose-Response Curve.

The present invention contemplates a high-throughput approach to screening compounds. FIG. 2 shows a representative cell proliferation dose-response curve of a lead compound (NSC191384) on J82 cells grown on SISgel and as non-confluent monolayers compiled after screening over 2000 compounds from two libraries of compounds with anti-cancer activity obtained from the National Institute of Health. The dose-response data confirms that the test compound is more active against cancer cells grown under the suppressing conditions than it is against cancer cells grown in conventional, non-suppressing cell culture (expressing malignant phenotypic characteristics) and drug screening.

FIGS. 3A and 3B show seven lead compounds (NSC191384, NSC 606532, NSC 697726, NSC140377, NSC191384D-1, NSC191384D-2, and NSC191384D-3) that have been identified having several fold increased sensitivity against cells on normal matrix than against cells grown on plastic.

Figure 5:
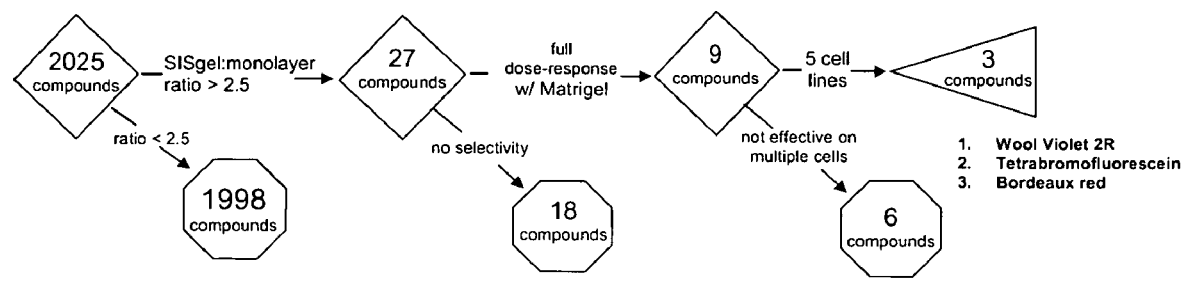
FIG. 5 is a flowchart showing results of a chemical library screen.

FIG. 5 is a flowchart showing results of a chemical library screen wherein additional lead compounds Wool Violet 2R, 3,4,5,6-tetrabromofluorescein, and Bordeaux Red have been identified.

FIGS. 6A-6C show representative cell proliferation dose-response curves of additional lead compounds Wool Violet 2R, 3,4,5,6-tetrabromofluorescein, and Bordeaux Red that have been identified having several fold increased sensitivity against cells on normal matrix than against cells grown on plastic.

FIG. 7 shows that the growth of cells in SISgel produced a significantly different phenotype than cells grown in Matrigel. Cells in SISgel grew as a monolayer and cells grown on Matrigel either forming a 3-dimensional lattice (MDA-MB-468) or grow in 3-dimensional sheets (B16-F10).

Figure 8:
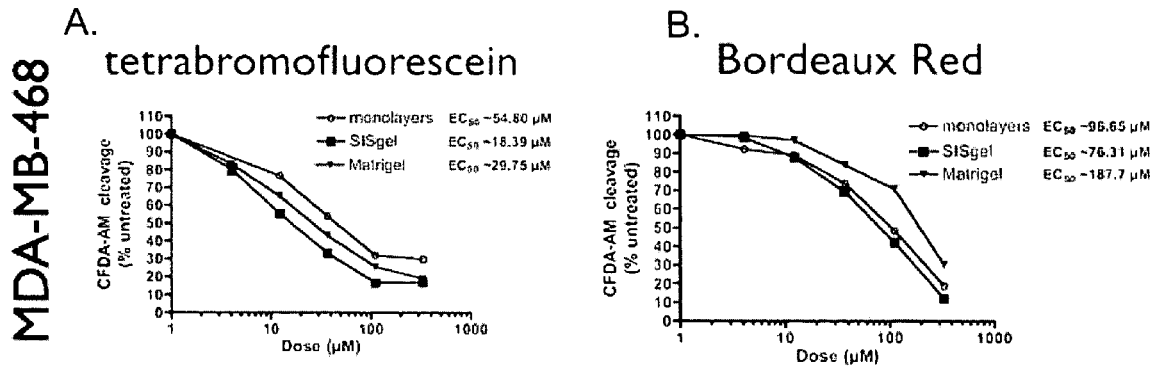
FIGS. 8A-8B are Full Dose-Response curves identifying two lead compounds for attacking suppressed MDA-MD-468 breast cancer cells.

FIGS. 8A and 8B show complete dose response relations of one of the lead compounds (tetrabromofluorescein) indicating that cells grown in SISgel were more sensitive to the lead compounds as indicated by lower $EC_{50}$ values (defined as the molar concentration of agonist, which produces 50% of the maximum possible response dose for that agonist) as compared to cells grown as monolayers or in Matrigel.

Figure 9:
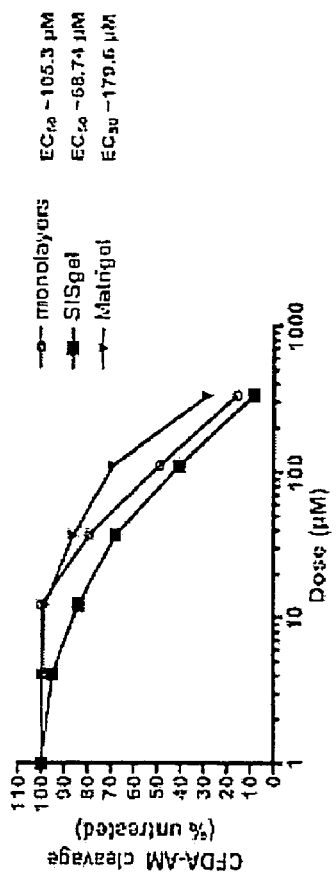
FIGS. 9A-9B are Full Dose-Response curves identifying two lead compounds for attacking suppressed B16-F10 melanoma cells.
Figure 9:
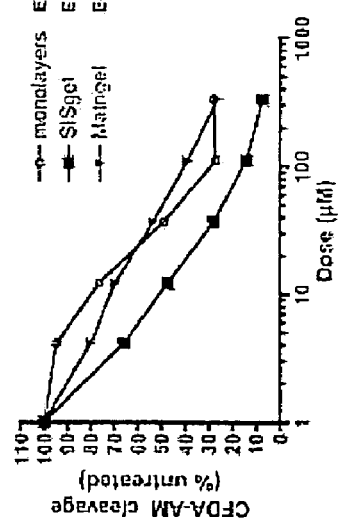

FIGS. 9A and 9B show complete dose response relations of another of the lead compounds (Bordeaux Red) indicating that cells grown in SISgel were more sensitive to the lead compounds as indicated by lower $EC_{50}$ values as compared to cells grown as monolayers or in Matrigel.

Utility

In addition to the screening method described above, the present invention further provides a method for the treatment of a patient afflicted with cancer or who may have suppressed metastatic cancer cells or conditions characterized at least wherein such disease states or conditions may be treated by the administration of a therapeutically effective amount of a compound of the present invention as described hereinabove to a subject in need thereof.

A therapeutically effective amount of a compound of the present invention refers to an amount which is effective in controlling, reducing, or suppressing the growth or expression of a cancer cell, particularly a suppressed metastatic cancer cell. The term "controlling" is intended to refer to all processes wherein there may be a slowing, suppressing, interrupting, arresting, or stopping of the progression of the disease and does not necessarily indicate a total elimination of all disease symptoms.

The term "therapeutically effective amount" is further meant to define an amount resulting in the improvement of any parameters or clinical symptoms characteristic of cancer. The actual dose will be different for the various specific molecules, and will vary with the patient's overall condition, the seriousness of the symptoms, and counter indications.

As used herein, the term "subject" or "patient" refers to a warm blooded animal such as a mammal which is afflicted with a particular cancer. It is understood that guinea pigs, dogs, cats, rats, mice, horses, cattle, sheep, zoo animals, llamas, livestock, and humans are examples of animals within the scope of the meaning of the term.

A therapeutically effective amount of the compound used in the treatment described herein can be readily determined by the attending diagnostician, as one of ordinary skill in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease or condition involved; the degree of or involvement or the severity of the disease or condition; the response of the individual subject; the particular compound administered; the mode of administration; the bioavailability characteristic of the preparation administered; the dose regimen selected; the use of concomitant medication; and other relevant circumstances.

A therapeutically effective amount of a compound of the present invention also refers to an amount of the compound which is effective in controlling, reducing or eliminating cancer or another condition described herein.

A therapeutically effective amount of the compositions of the present invention will generally contain sufficient active ingredient (e.g., NSC 191384, NSC 191384D-1, NSC 191384D-2, NSC 191384D-3, NSC 606532, NSC 697726, and NSC140377 shown in FIGS. 3A and 3B, and Wool Violet 2R, 3,4,5,6-tetrabromofluorescein, and Bordeaux Red shown in FIGS. 6A-6C) (or any salt, ester, or derivative thereof) to deliver from about 0.1 µg/kg to about 100 mg/kg (weight of active ingredient/body weight of patient). Preferably, the composition will deliver at least 0.5 µg/kg to 50 mg/kg, and more preferably at least 1 µg/kg to 10 mg/kg.

Practice of the method of the present invention comprises administering to a subject a therapeutically effective amount of the active ingredient, in any suitable systemic or local formulation, in an amount effective to deliver the dosages listed above. An effective, particularly preferred dosage of a positive compound (for example, NSC 191384, NSC 191384D-1, NSC 191384D-2, NSC 191384D-3, NSC 606532, NSC 697726, NSC140377, Wool Violet 2R, 3,4,5,6-tetrabromofluorescein, and Bordeaux Red) for substantially inhibiting suppressed cancer cells is 1 l/kg to 1 mg/kg of the active ingredient. The dosage can be administered on a one-time basis, or (for example) from one to five times per day or once or twice per week, or continuously via a venous drip, depending on the desired therapeutic effect.

As noted, preferred amounts and modes of administration are able to be determined by one of ordinary skill in the art. One of ordinary skill in the art of preparing formulations can readily select the proper form and mode of administration depending upon the particular characteristics of the compound selected, the disease state to be treated, the stage of the disease, and other relevant circumstances using formulation technology known in the art, described, for example, in *Remington's Pharmaceutical Sciences*, latest edition, Mack Publishing Co.

Pharmaceutical compositions can be manufactured utilizing techniques known in the art. Typically the therapeutically effective amount of the compound will be admixed with a pharmaceutically acceptable carrier.

The compounds or compositions of the present invention may be administered by a variety of routes, for example, orally, intrarectally, or parenterally (i.e., subcutaneously, intravenously, intramuscularly, intraperitoneally, or intratracheally).

For oral and intrarectal administration, the compounds can be formulated into solid or liquid preparations such as capsules, suppositories, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of this invention can be tabletted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety. Topical administration is also intended to refer to intrarectal administration which causes a topical effect on the intraluminal surface.

As noted above, the compositions can also include an appropriate carrier. For topical use, any of the conventional excipients may be added to formulate the active ingredients into a lotion, ointment, powder, cream, spray, or aerosol. For surgical implantation, the active ingredients may be combined with any of the well-known biodegradable and bioerodible carriers, such as polylactic acid and collagen formulations. Such materials may be in the form of solid implants, sutures, sponges, wound dressings, and the like. In any event, for local use of the materials, the active ingredients will usually be present in the carrier or excipient in a weight ratio of from about 1:1000 to 1:20,000, but are not limited to ratios within this range. Preparation of compositions for local use are detailed in *Remington's Pharmaceutical Sciences*, latest edition, (Mack Publishing).

Additional pharmaceutical methods may be employed to control the duration of action. Increased half-life and controlled release preparations may be achieved through the use of polymers to conjugate, complex with, or absorb the anticancer compounds described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide, and the appropriate concentration of macromolecules as well as the methods of incorporation in order to control release.

For example, the duration of action of the drugs by use of controlled release preparations may be accomplished by incorporation of the test compound or its functional derivatives into particles of a polymeric material such as polyesters, polyamides, polyamino acids, hydrogels, poly(lactic acid), ethylene vinylacetate copolymers, copolymer micelles of, for example, PEG and poly(1-aspartamide).

The half-life of the test compounds described herein can be extended by their being conjugated to other molecules such as polymers using methods known in the art to form drug-polymer conjugates. For example, the test compounds can be bound to molecules of inert polymers known in the art, such as a molecule of polyethylene glycol (PEG) in a method known as "pegylation". Pegylation can therefore extend the in vivo lifetime and thus therapeutic effectiveness of the test compound. Pegylation also reduces the potential antigenicity of the test compound. Pegylation can also enhance the solubility of the test compound thereby improving their therapeutic effect. PEGs used may be linear or branched-chain.

PEG molecules can be modified by functional groups, for example as shown in Harris, et al., "Pegylation, A Novel Process for Modifying Phararmacokinetics", *Clin Pharmacokinet,* 2001:40(7); 539-551, and a functional group of the compound can be linked thereto, wherein the PEG molecule can carry one or a plurality of one or more types of anti-cancer compounds.

By "polyethylene glycol" or "PEG" is meant a polyalkylene glycol compound or a derivative thereof, with or without coupling agents or derviatization with coupling or activating moeities (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the present invention. Other appropriate polymer conjugates include, but are not limited to, non-polypeptide polymers, charged or neutral polymers of the following types: dextran, colominic acids or other carbohydrate based polymers, biotin derivatives and dendrimers, for example. The term PEG is also meant to include other polymers of the class polyalkylene oxides.

The PEG can be linked to the anti-cancer compound by any means known in the art, such as by a covalent bond, to a side group, or functional group of the compound including, amine, thio, or carboxyl groups.

The PEG moiety attached to the protein may range in molecular weight from about 200 to 20,000 MW. Preferably the PEG moiety will be from about 1,000 to 8,000 MW, more preferably from about 3,250 to 5,000 MW, most preferably about 5,000 MW.

The actual number of PEG molecules covalently bound per anti-cancer compound of the invention may vary widely depending upon the desired stability (i.e., serum half-life) of the pegylated compound.

Molecules contemplated herein can be linked to PEG molecules using techniques shown, for example (but not limited to), in U.S. Pat. Nos. 4,179,337; 5,382,657; 5,972,885; 6,177,087; 6,165,509; 5,766,897; and 6,217,869; the specifications and drawings each of which are hereby expressly incorporated herein by reference.

Alternatively, it is possible to entrap the test compounds in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in the latest edition of *Remington's Pharmaceutical Sciences.*

U.S. Pat. No. 4,789,734 describes methods for encapsulating biochemicals in liposomes and is hereby expressly incorporated by reference herein. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine,* pp. 287-341 (Academic Press, 1979). Microspheres formed of polymers or proteins are well known to those skilled in the art, and can be tailored for passage through the gastrointestinal tract directly into the blood stream. Alternatively, the agents can be incorporated and the microspheres, or composite of microspheres, implanted for slow release over a period of time, ranging from days to months. See, for example, U.S. Pat. Nos. 4,906,474; 4,925,673; and 3,625,214 which are incorporated by reference herein.

When the composition is to be used as an injectable material, it can be formulated into a conventional injectable carrier. Suitable carriers include biocompatible and pharmaceutically acceptable phosphate buffered saline solutions, which are preferably isotonic.

For reconstitution of a lyophilized product in accordance with this invention, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

The compounds can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the compounds of the invention may be incorporated into pharmaceutical preparations which may be used for therapeutic purposes. However, the term "pharmaceutical preparation" is intended in a broader sense herein to include preparations containing a test compound composition in accordance with this invention, used not only for therapeutic purposes but also for reagent, screening, or diagnostic purposes as known in the art, or for tissue culture. The pharmaceutical preparation intended for therapeutic use should contain a "pharmaceutically acceptable" or "therapeutically effective amount" of a test compound, i.e., that amount necessary for preventative or curative health measures. If the pharmaceutical preparation is to be employed as a reagent or diagnostic, then it should contain reagent or diagnostic amounts of a test compound.

All of the assay methods listed herein are well within the ability of one of ordinary skill in the art given the teachings provided herein.

The present invention is not to be limited in scope by the specific embodiments described herein, since such embodiments are intended as but single illustrations of one aspect of the invention any functionally equivalent embodiments are within the scope of this invention. Indeed, various modifications of the methods of the invention in addition to those shown and described herein will become apparent to those skilled in the art from the foregoing description.

The invention claimed is:

1. A method of identifying a compound which is able to target suppressed micrometastatic cancer cells in favor of non-suppressed micrometastatic cancer cells, comprising:
   providing a suppressed cancer cell culture comprising actively growing cancer cells which have a malignant phenotype, wherein the malignant phenotype of the cancer cells is suppressed by a malignant phenotype-suppressing matrix;
   providing a non-suppressed cancer cell culture comprising actively growing cancer cells which have the malignant phenotype, wherein the malignant phenotype of the cancer cells is expressed;
   treating each of the suppressed cancer cell culture and the non-suppressed cancer cell culture with a test compound and incubating said treated suppressed and non-suppressed cancer cell cultures; and
   measuring a first quantity related to the number or survival of cancer cells in the treated suppressed cancer cell culture and measuring a second quantity related to the number or survival of cancer cells in the treated non-suppressed cancer cell culture and wherein when the second quantity exceeds the first quantity the test compound is shown to target suppressed micrometastatic cancer cells in favor of non-suppressed micrometastatic cancer cells.

2. A method of identifying a compound which is able to target suppressed micrometastatic cancer cells in favor of non-suppressed micrometastatic cancer cells, the method comprising the steps of:
   in a first cell culture system, providing a suppressing cell support matrix which causes suppression of a malignant phenotype in a growing cancer cell;
   combining a quantity of cancer cells with the suppressing cell support matrix forming a suppressing matrix-cell mixture;
   incubating the suppressing matrix-cell mixture to form a suppressed cancer cell culture;
   adding a test compound to the suppressed cancer cell culture forming a treated suppressed culture;
   incubating the treated suppressed culture to form an incubated treated suppressed culture;
   in a second cell culture system, providing a non-suppressing cell support matrix which causes expression of a malignant phenotype in a growing cancer cell;
   combining a second quantity of the cancer cells with the non-suppressing cell support matrix forming a non-suppressing matrix-cell mixture;
   incubating the non-suppressing matrix-cell mixture to form a non-suppressed cancer cell culture;
   adding a test compound to the non-suppressed cancer cell culture forming a treated non-suppressed culture;
   incubating the non-suppressed test culture to form an incubated treated non-suppressed culture; and
   measuring a first quantity related to the number or survival of cells in the incubated treated suppressed culture and measuring a second quantity related to the number or survival of cells in the incubated treated non-suppressed culture and wherein when the second quantity exceeds the first quantity the test compound is shown to target suppressed micrometastatic cancer cells in favor of non-suppressed micrometastatic cancer cells.

3. The method of claim 2 wherein the cancer cells are selected from the group consisting of bladder cells, liver cells, breast cells, lung cells, prostate cells, colon cells, skin cells, transitional cells, squamous cells, small cells, medulary cells, cells of adenocarcinomas, and cells of basal cell carcinomas.

4. The method of claim 2 further comprising the step of confirming the test compound's ability to target suppressed micrometastatic cancer cells via a full-dose response curve performed in a cancer-derived non-suppressing extracellular matrix preparation for screening for increased activity of the test compound when compared to the test compound's activity in the suppressing cell support matrix.

5. The method of claim 4 wherein the non-suppressing cell support matrix is Matrigel.

6. The method of claim 4 wherein the non-suppressing cell support matrix is plastic.

7. The method of claim 2 wherein the non-suppressing cell support matrix is plastic.

8. The method of claim 2 wherein the non-suppressing cell support matrix is Matrigel.

9. The method of claim 2 the first quantity and second quantity are measured by a fluorometric method.

10. A method of identifying a compound which is able to target suppressed micrometastatic cancer cells in favor of non-suppressed micrometastatic cancer cells, the method comprising the steps of:
   in a first cell culture system, providing a suppressing cell support matrix which causes suppression of a malignant phenotype in a growing cancer cell;
   providing a cell-nutrient mixture comprising a quantity of cancer cells disposed in a nutrient;
   combining a first portion of the cell-nutrient mixture with the suppressing cell support matrix forming a suppressing matrix-cell mixture;
   incubating the suppressing matrix-cell mixture for a period of time to allow growth while causing suppression of the malignant phenotype in the cancer cells thereby forming a suppressed cancer cell culture;
   adding a quantity of a test compound to the suppressed cancer cell culture forming a treated suppressed culture;
   incubating the treated suppressed culture for a predetermined length of time forming an incubated treated suppressed culture;
   in a second cell culture system, providing a non-suppressing cell support matrix which causes expression of a malignant phenotype in a growing cancer cell;
   combining a second portion of the cell-nutrient mixture with the non-suppressing cell support matrix forming a non-suppressing matrix-cell mixture;

incubating the non-suppressing matrix-cell mixture for a period of time to allow growth and expression of the malignant phenotype in the cancer cells thereby forming non-suppressed cancer cell culture;

adding a quantity of a test compound to the non-suppressed cancer cell culture forming a treated non-suppressed culture;

incubating the treated non-suppressed culture for a predetermined length of time forming an incubated treated non-suppressed culture; and measuring a first quantity related to the number or survival of cells in the incubated treated suppressed culture and measuring a second quantity related to the number or survival of cells in the incubated treated non-suppressed culture and wherein when the second quantity exceeds the first quantity the test compound is shown to target suppressed micrometastatic cancer cells in favor of non-suppressed micrometastatic cancer cells.

11. The method of claim 10 wherein the cancer cells in the cell-nutrient mixture are selected from the group consisting of bladder cells, liver cells, transitional cells, squamous cells, small cells, medulary cells, cells of adenocarcinomas, and cells of basal cell carcinomas.

12. A method of identifying a compound which is able to preferentially target cancer cells having a suppressed malignant phenotype in favor of cancer cells having a non-suppressed malignant phenotype, comprising:

providing a suppressed cancer cell culture comprising actively growing cancer cells which have a malignant phenotype, wherein the malignant phenotype of the cancer cells is suppressed by growth of the cancer cells on an extracellular matrix derived from normal cells;

providing a non-suppressed cancer cell culture comprising actively growing cancer cells which have the malignant phenotype, wherein the malignant phenotype of the cancer cells is expressed and wherein the non-suppressed cancer cell culture is grown on a plastic matrix;

treating each of the suppressed cancer cell culture and the non-suppressed cancer cell culture with a test compound and incubating said treated suppressed and non-suppressed cancer cell cultures; and measuring a first quantity related to the number or survival of cancer cells in the treated suppressed cancer cell culture and measuring a second quantity related to the number or survival of cancer cells in the treated non-suppressed cancer cell culture and wherein when the second quantity exceeds the first quantity the test compound is demonstrated to target cancer cells having a suppressed malignant phenotype in favor of cancer cells having a non-suppressed malignant phenotype.

13. The method of claim 12 wherein the cancer cells are selected from the group consisting of bladder cells, liver cells, breast cells, lung cells, prostate cells, colon cells, skin cells, transitional cells, squamous cells, small cells, medulary cells, cells of adenocarcinomas, and cells of basal cell carcinomas.

14. The method of claim 12 further comprising the step of confirming the test compound's ability to preferentially target suppressed cancer cells versus non-suppressed cancer cells via a full-dose response curve performed in a non-suppressing extracellular matrix derived from cancer cells.

15. The method of claim 12 the first quantity and second quantity are measured by a fluorometric method.

* * * * *

UNITED STATES PATENT AND TRADEMARK OFFICE
CERTIFICATE OF CORRECTION

PATENT NO. : 7,575,926 B1  Page 1 of 1
APPLICATION NO. : 11/642313
DATED : August 18, 2009
INVENTOR(S) : Robert E. Hurst et al.

It is certified that error appears in the above-identified patent and that said Letters Patent is hereby corrected as shown below:

Column 3, line 60: After "growth of" delete "382" and replace with -- J82 --.

Column 9, line 56: After "cell is" delete "1 1/kg" and replace with -- 1 µg/kg --.

Signed and Sealed this

Sixth Day of October, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,575,926 B1 | Page 1 of 1 |
| APPLICATION NO. | : 11/642313 | |
| DATED | : August 18, 2009 | |
| INVENTOR(S) | : Robert E. Hurst, Michael A. Ihnat and Kimberly D. Kyker | |

It is certified that error appears in the above-identified patent and that said Letters Patent is hereby corrected as shown below:

Column 1, lines 18-21: Delete entirety of paragraph and replace with -- This invention was made with government support under Contract Numbers CA075822 and DK069808 awarded by the National Institutes of Health (NIH). The government has certain rights in the invention. --

Signed and Sealed this

Twenty-ninth Day of November, 2011

David J. Kappos
*Director of the United States Patent and Trademark Office*